US00PP32083P3

(12) United States Plant Patent
Lovengreen Ferreira

(10) Patent No.: US PP32,083 P3
(45) Date of Patent: Aug. 18, 2020

(54) ***ARISTOTELIA* PLANT NAMED 'PRETORIA'**

(50) Latin Name: *Aristotelia chilensis*
Varietal Denomination: Pretoria

(71) Applicant: Royal Super Fruits B.V., Katwijk aan Zee (NL)

(72) Inventor: Axel Lovengreen Ferreira, Pitrufquen (CL)

(73) Assignee: ROYAL SUPER FRUITS B.V., Katwijk aan Zee (NL)

( * ) Notice: Subject to any disclaimer, the term of this patent is extended or adjusted under 35 U.S.C. 154(b) by 0 days.

(21) Appl. No.: 16/602,063

(22) Filed: Jul. 29, 2019

(65) Prior Publication Data

US 2020/0037486 P1 Jan. 30, 2020

(30) Foreign Application Priority Data

Jul. 30, 2018 (QZ) ..... PBR 2018/1981

(51) Int. Cl.
*A01H 5/00* (2018.01)
*A01H 6/00* (2018.01)
*A01H 5/12* (2018.01)

(52) U.S. Cl.
USPC ..... Plt./216
CPC ..... *A01H 6/00* (2018.05); *A01H 5/12* (2013.01)

(58) Field of Classification Search
USPC ..... Plt./216
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Aristotelia chilensis* plant named 'Pretoria' that is characterized by its vigorous evergreen plant habit and its slightly glossy leaves that are dark blue-green in color.

2 Drawing Sheets

Botanical classification: *Aristotelia chilensis*.
Varietal denomination: 'Pretoria'.

CROSS REFERENCE TO RELATED APPLICATIONS

This application is co-pending with a U.S. Plant Patent Applications filed for a plant derived from the same breeding program that are entitled *Aristotelia* Plant Named 'AZ50' (U.S. Plant patent application Ser. No. 16/602,061), *Aristotelia* Plant Named 'Sobresale' (U.S. Plant patent Ser. No. 16/602,062), and *Aristotelia* Plant Named 'VB1' (U.S. Plant patent Ser. No. 16/602,064).

BACKGROUND OF THE INVENTION

The present invention relates to a new and distinct cultivar of *Aristotelia chilensis* and will be referred to hereafter by its cultivar name, 'Pretoria'. 'Pretoria' represents a perennial evergreen shrub grown for landscape use.

'Pretoria' was discovered by the Inventor as a chance seedling in a trial garden in Pitrufquen, IX region de la Araucanía, Chile in January of 2017. The field had been planted with numerous unnamed proprietary seedling plants from the Inventor's breeding program. The parentage is therefore unknown.

Asexual propagation of the new cultivar was first accomplished by softwood stem cuttings by the Inventor in summer of 2017 in Pitrufquen, IX region de la Araucanía, Chile. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pretoria' as a unique cultivar of *Aristotelia chilensis*.

1. 'Pretoria' exhibits a vigorous evergreen plant habit.
2. 'Pretoria' exhibits slightly glossy leaves that are dark blue-green in color.

'Pretoria' can be most closely compared to the *Aristotelia chilensis* cultivars 'Variegata' (not patented), 'AZ50', 'Sobresale', and 'VB1'. 'Variegata' differs from 'Pretoria' in having leaves that are lighter green in color and variegated. 'AZ50' differs from 'Pretoria' in having young foliage that is yellow-green, mature foliage that is dark green in color and a more open plant habit. 'Sobresale' differs from 'Pretoria' in having a slightly narrower plant shape, more yellow-green colored young stems, yellow-green young foliage and more glossy mature foliage that is dark green in color. 'VB1' differs from 'Pretoria' in having yellow-green branches and yellow-green young foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new

*Aristotelia*. The photographs were taken of a 24-month-old plant (after a single pruning 3 weeks prior) of 'Pretoria' as grown in an unheated greenhouse in a 27-cm container in Boskoop, The Netherlands.

Figure 1:
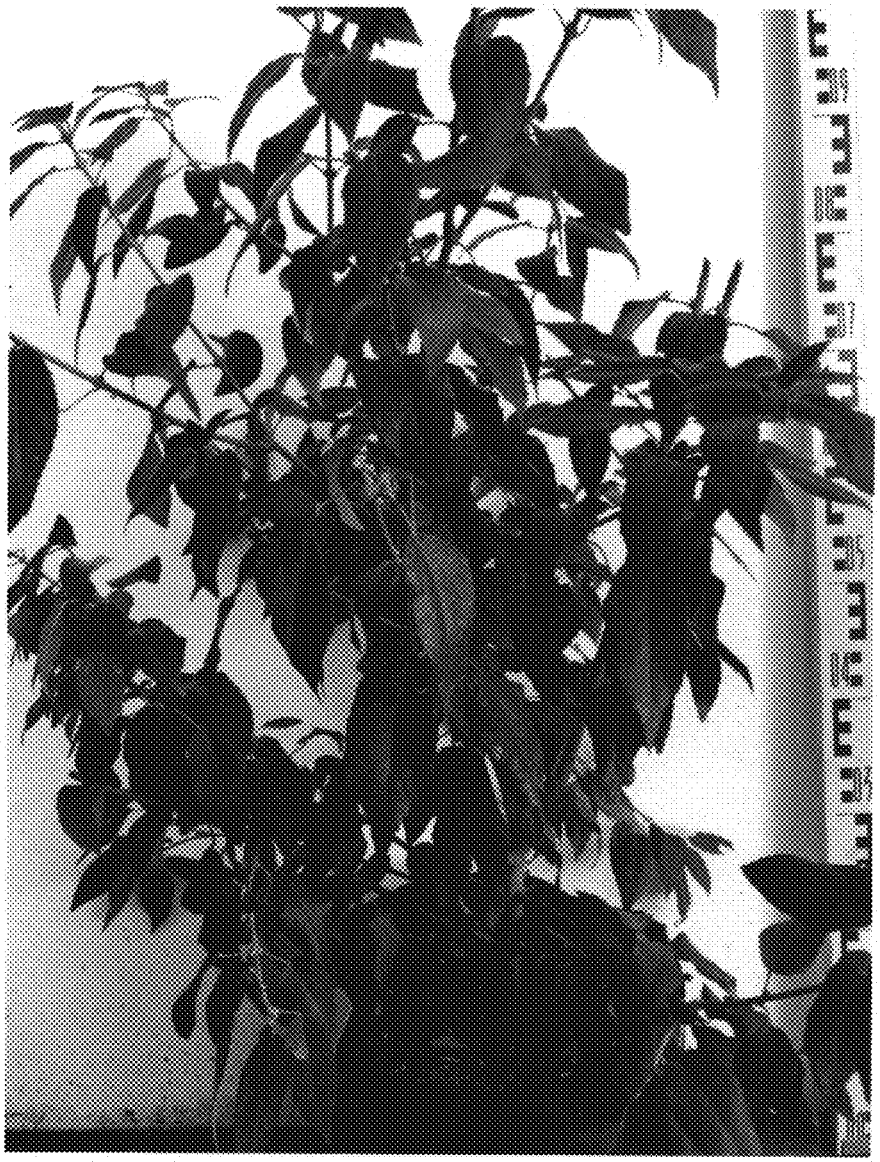

The photograph in FIG. 1 provides a view of the plant habit of 'Pretoria'.

Figure 2:
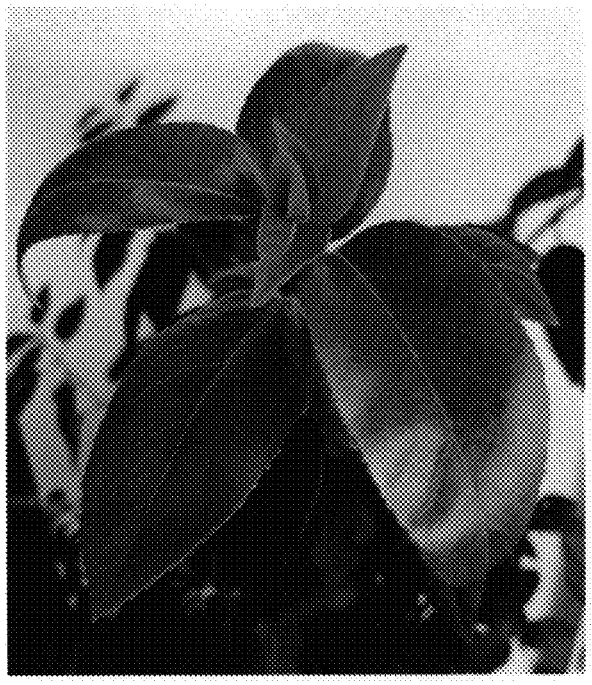

The photograph in FIG. 2 provides a close up view of the young foliage of 'Pretoria'.

Figure 3:
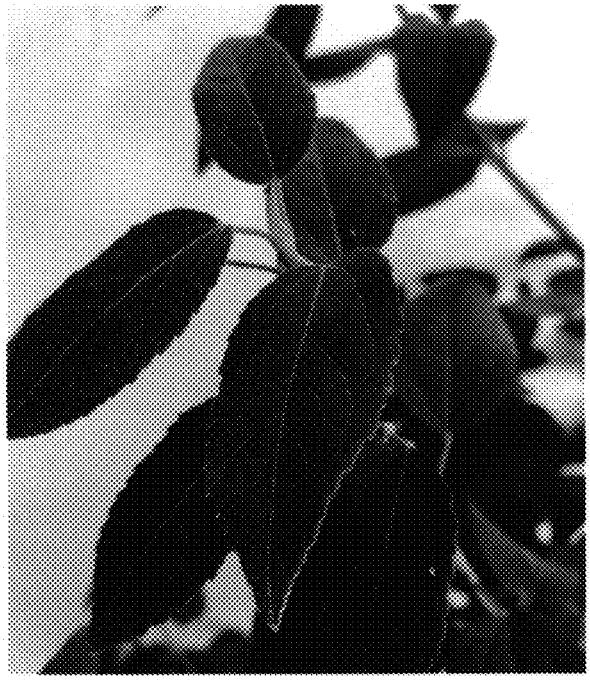

The photograph in FIG. 3 provides a close-up view of the mature foliage of 'Pretoria'.

The colors in the photographs are as close as possible with the photographic and printing technology utilized and the color values cited in the detailed botanical description accurately describe the colors of the new *Aristotelia*.

BOTANICAL DESCRIPTION OF THE PLANT

The following is a detailed description of 24-month-old plants of 'Pretoria' as grown in an unheated greenhouse in 27-cm containers in Noordwijkerhout, The Netherlands (after a single pruning 3 weeks prior). The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Perennial, evergreen shrub.

*Plant habit*.—Obovate.

*Height and spread*.—An average of 96 cm in in height and 49.8 cm in spread, reaches 3 m in height and 2.5 m in spread as a mature plant in the landscape.

*Cold hardiness*.—At least in U.S.D.A. Zones 8.

*Diseases and pests*.—No susceptibility and resistance to diseases or pests has been observed.

*Root description*.—Fine and fibrous.

*Propagation*.—Softwood stem cuttings.

*Root development*.—An average of 60 days for root initiation with a young rooted plant produced in an average of 4 months.

*Growth rate and vigor*.—Moderate.

Stem description:

*Stem shape*.—Rounded.

*Stem strength*.—Strong.

*Stem color*.—Young; 143C, mature; 146A, occasionally tinged 197A, internodes; 146A, occasionally tinged 197A, old bark; NN137C to NN137D.

*Stem size*.—An average of 25.5 cm in length and 2.75 mm in diameter.

*Stem surface*.—Young and mature; slightly glossy and covered with a very thin wax layer, 188C in color, old bark; densely covered with lenticels, an average of 1.5 mm in length, 157A in color.

*Stem aspect*.—Average angle of vertical to 45°, varying between 40° and 50°.

*Internode length*.—An average of 4.5 cm.

*Branching*.—Freely branching with an average of 1 main branch and 20 lateral branches.

Foliage description:

*Leaf shape*.—Ovate to narrow ovate.

*Leaf arrangement*.—Opposite to near opposite.

*Leaf aspect*.—Moderately to strongly undulate.

*Leaf division*.—Simple.

*Leaf base*.—Obtuse to acute.

*Leaf apex*.—Acute to bluntly acute.

*Leaf margins*.—Serrate.

*Leaf venation*.—Pinnate, color; upper surface N148D, lower surface 145A to 145B.

*Leaf size*.—An average of 11.9 cm in length and 5.5 cm in width.

*Leaf attachment*.—Petiolate.

*Leaf number*.—An average of 12 (6 pairs).

*Leaf surface*.—Upper surface; smooth and glabrous, lower surface; smooth and glabrous with small tufts of hairs on the vein axils.

*Leaf color*.—Young foliage; upper surface NN137A, young lower surface 146B, mature foliage; upper surface between 147A and N189A, covered with a very thin waxy layer 188A, mature lower surface NN137D.

*Petioles*.—An average of 2.9 cm in length and 2 mm in diameter, strong, upper surface color 178A, lower surface color 145A and slightly tinged with 178A, upper surface matte, lower surface slightly glossy and slightly to moderately pubescent with hairs an average of 0.3 mm in length and too small to measure color.

Inflorescence description: No flower production produced to date on plants available for data collection.

Fruit and seed: No production observed to date on plants available for data collection.

It is claimed:

1. A new and distinct cultivar of *Aristotelia* plant named 'Pretoria' substantially as herein illustrated and described.

* * * * *